United States Patent [19]

Nagase et al.

[11] Patent Number: 5,624,680
[45] Date of Patent: Apr. 29, 1997

[54] HYDROXYSILYL-TERMINATED POLYOXYETHYLENE COMPOUND, QUATERNARY-SALT-TERMINATED BLOCK COPOLYMER, AND PERCUTANEOUS ABSORPTION-PROMOTING AGENT

[75] Inventors: Yu Nagase, Sagamihara; Takao Aoyagi, Nagareyama; Tomoko Akimoto, Zama, all of Japan

[73] Assignee: Sagami Chemical Research Center, Sagamihara, Japan

[21] Appl. No.: 537,867

[22] PCT Filed: Jul. 7, 1994

[86] PCT No.: PCT/JP94/01109

§ 371 Date: Jan. 23, 1996

§ 102(e) Date: Jan. 23, 1996

[87] PCT Pub. No.: WO95/03352

PCT Pub. Date: Feb. 2, 1995

[30] Foreign Application Priority Data

Jul. 23, 1993 [JP] Japan ..................... 5-201966

[51] Int. Cl.$^6$ .................................. A61F 13/02

[52] U.S. Cl. .................. 424/448; 424/449; 514/946; 514/947; 556/423; 556/425; 528/14; 528/15; 528/21; 528/28

[58] Field of Search ................... 528/15, 28, 14, 528/21; 556/423, 425; 514/946, 947; 424/448, 449

[56] References Cited

U.S. PATENT DOCUMENTS

| | | | |
|---|---|---|---|
| 5,087,715 | 2/1992 | Snow | 556/423 |
| 5,200,488 | 4/1993 | Nagase et al. | 528/28 |

*Primary Examiner*—Melvyn I. Marquis
*Attorney, Agent, or Firm*—Oblon, Spivak, McClelland, Meier & Neustadt, P.C.

[57] ABSTRACT

A hydrosilyl-terminated polyoxyethylene compound of the general formula (I), a quaternary-salt-terminated polyoxyethylene/polyorganosiloxane block copolymer of the general formula (II) derived from the above compound, and a percutaneous drug absorption promoter comprising the above copolymer (II). The copolymer is usable as a percutaneous absorption promoter having a good drug absorption promoting effect and being effective for various drugs.

6 Claims, No Drawings

HYDROXYSILYL-TERMINATED POLYOXYETHYLENE COMPOUND, QUATERNARY-SALT-TERMINATED BLOCK COPOLYMER, AND PERCUTANEOUS ABSORPTION-PROMOTING AGENT

TECHNOLOGICAL FIELD

The present invention relates to a hydroxysilyl-terminated polyoxyethylene compound, of the following formula

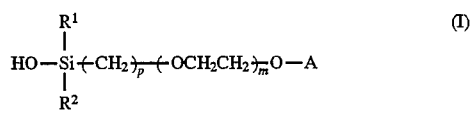

wherein, each of $R^1$ and $R^2$ which may be the same or different, is a $C_{1-6}$ alkyl group or a phenyl group; A is an alkyl group or a group represented by $-(CH_2)_p-SiR^1R^2OH$; p is an integer of from 2 to 6; an average value of degree of polymerization, m, is a real number of from 3 to 100, and a quaternary-salt-terminated polyoxyethylene/polyorganosiloxane block copolymer, of the following formula (II):

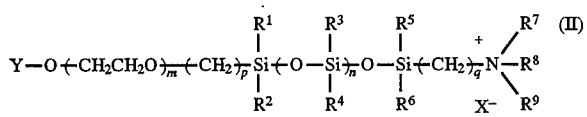

wherein, each of $R^1$ to $R^6$ which may be the same or different, is a $C_{1-6}$ alkyl group or a phenyl group; each of $R^7$ to $R^9$ which may be the same or different, is an alkyl group, a substituted alkyl group or a phenyl group, or two or three of $R^7$ to $R^9$ and the nitrogen atom connected thereto together may form a heterocycle containing a nitrogen; $X^-$ is a counter anion in the quaternary salt; Y is an alkyl group or a quaternary-salt-terminated polyorganosiloxane chain represented by the following formula (III):

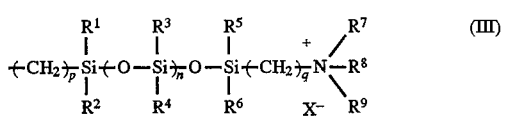

where p is an integer of from 2 to 6; q is an integer of from 1 to 6; an average value of degree of polymerization, m or n, is a real number of from 3 to 100; each of $R^3$ and $R^4$ may be the same or different in each of the repeating unit. The present invention also provides an agent for promoting percutaneous absorption of a drug, which comprises said quaternary-salt-terminated polyoxyethytene/polyorganosiloxane block copolymer.

BACKGROUND ART

Studies have been actively conducted on drug delivery systems (DDS) for the purpose of efficiently delivering drugs to desired sites and avoiding side effects. Among them, a percutaneous absorption system wherein the skin is the application site of a drug, has attracted an attention in recent years. The merit of this system include ∗ @ it is thereby possible to avoid the first-pass effect at the liver, ∗ A the percutaneous penetration rate of the drug can be controlled so that a long active constant drug level can be maintained, ∗B the administration is not influenced by foods or vomiting, ∗C the administration can easily be adjusted, and ∗D the drug can be administered in the vicinity of the desired site. However, it still has drawbacks such that ∗ @ the application is limited to a drug, the dose of which is relatively small, ∗A useful drugs are relatively limited, ∗B there is a possibility that deterioration of the keratin layer or a skin allergy reaction is thereby promoted, and ∗C no rapid action can be expected. Under these circumstances, a combined use of a percutaneous absorption-promoting agent is being studied to overcome such drawbacks.

For example, it has been pointed out in Journal of Controlled Release, Vol. 25, pp. 1–22 (1993) that a variety of low-molecular-weight compounds are effective as percutaneous absorption-promoting agents, with describing abstracts of patents with respect to dimethylsulfoxide, 1-alkylpyrrolidone derivatives, 1-dodecylazacycloheptan-2-on, and the like. The present inventors have proposed, as percutaneous absorption-promoting agents having low toxicity and irritation to the skin, polymeric compounds such as a polymer containing a benzalkonium salt in its side chain (Journal of Controlled Release, Vol. 13. pp.63–71 (1990)), a polymer containing a pyridinium salt in its side chain (Polymer, Vol. 32, No. 11, 2106–2111 (1991)), a polyorganosiloxane containing a N-methylpyridinium salt in its one terminal (Polymer, Vol. 33, No. 10, 2203–2207 (1992)), and a polyorganosiloxane containing a pyridinium or an ammonium salt in its one terminal (EP-0484857A, U.S. Pat. No. 5,200,488).

Among the above promoting agents, however, particularly low-molecular-weight compounds such as dimethylsulfoxide, 1-alkylpyrrolidone derivatives and 1-dodecylazacycloheptan-2-on, had problems at practical application in that they have a toxicity or irritation toward a skin. On the other hand, all the above polymeric compounds proposed by the present inventors exhibited excellent promoting action accompanied with low toxicity and low irritation toward a skin, since they do not penetrate into the interior of the skin owing to the polymeric nature. Especially, the polyorganosiloxane containing a pyridinium or an ammonium salt at its one terminal comprises a polysiloxane chain which is inactive to a living body, and thus its toxicity is very low. However, these conventional polysiloxane type promoting agents have a problem that they are extremely effective for the percutaneous absorption of hydrophobic drugs, but the promoting effect reduces by half in the case of hydrophilic drugs. Therefore, these promoting agents are only applicable to limited drugs.

DISCLOSURE OF INVENTION

The present inventors have made extensive studies to solve the above problem, and especially to obtain a percutaneous absorption-promoting agent which is also effective for promoting the absorption of hydrophilic drugs. As a result, they have found that a novel hydroxysilyl-terminated polyoxyethylene compound can be synthesized, and a quaternary-salt-terminated polyoxyethylene/polyorganosiloxane block copolymer, which is readily derived from the above compound, exhibits excellent promoting effects for the percutaneous absorption of not only hydrophobic drugs but also hydrophilic drugs. The present invention has been accomplished on the basis of these discoveries.

Thus, the present invention provides a hydroxysilyl-terminated polyoxyethylene compound, of the following formula (I):

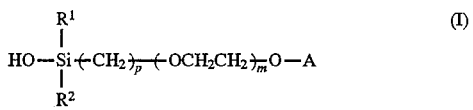

$$\text{HO}-\underset{R^2}{\overset{R^1}{\underset{|}{\overset{|}{Si}}}}-(\text{CH}_2)_p-(\text{OCH}_2\text{CH}_2)_m-\text{O}-\text{A} \qquad (I)$$

wherein, each of $R^1$ and $R^2$ which may be the same or different, is a $C_{1-6}$ alkyl group or a phenyl group; A is an alkyl group or a group represented by $-(\text{CH}_2)_p-\text{SiR}^1\text{R}^2\text{OH}$; p is an integer of from 2 to 6; an average value of degree of polymerization, m, is a real number of from 3 to 100, and a quaternary-salt-terminated polyoxyethylene/polyorganosiloxane block copolymer derived therefrom, of the following formula (II):

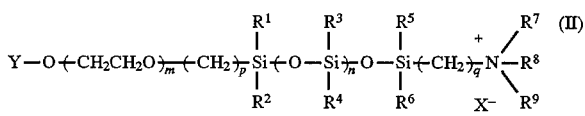

wherein, each of $R^1$ to $R^6$ which may be the same or different, is a $C_{1-6}$ alkyl group or a phenyl group; each of $R^7$ to $R^9$ which may be the same or different, is an alkyl group, a substituted alkyl group or a phenyl group, or two or three of $R^7$ to $R^9$ and the nitrogen atom connected thereto together may form a heterocycle containing a nitrogen; $X^-$ is a counter anion in the quaternary salt; Y is an alkyl group or a quaternary-salt-terminated polyorganosiloxane chain represented by the following formula (III):

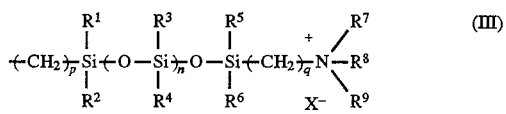

where p is an integer of from 2 to 6; q is an integer of from 1 to 6; an average value of degree of polymerization, m or n, is a real number of from 3 to 100; each of $R^3$ and $R^4$ may be the same or different in each of the repeating unit. The present invention also provides the use of such a block copolymer as an agent for promoting percutaneous absorption of a drug.

The present invention also provides a preparation for percutaneous absorption of a drug, which contain the drug, an effective amount of polyoxyethylene/polyorganosiloxane block copolymer of the present invention, and a pharmaceutically acceptable carrier, an additive or a combination thereof.

Furthermore, the present invention provides a method of promoting the absorption of a drug through a dermis or a mucous membrane by applying a composition obtainable by mixing a drug, an effective amount of polyoxyethylene/polyorganosiloxane block copolymer of the present invention, and a pharmaceutically acceptable carrier, an additive or a combination thereof.

The substituent represented by each of $R^1$ to $R^6$ in the above formulas (I), (II) and (III) may be an alkyl group such as a methyl group, an ethyl group, a propyl group, a butyl group, a pentyl group, a hexyl group, an isopropyl group or a t-butyl group, or a phenyl group. However, a methyl group is most preferred among the above substituents, from the viewpoint of easiness in the synthesis and the characteristics of the polysiloxane chain in the quaternary-salt-terminated block copolymer of the above formula (II) in the case of using as a percutaneous absorption-promoting agent. The counter anion in the quaternary salt represented by $X^-$ in the above formulas (II) and (III), may be a conjugate base of a Brenstead base, for example, a halogen ion such as $F^-$, $Cl^-$, $Br^-$ or $I^-$, a hydroxy ion, a conjugate base of a mineral acid such as a carbonate ion, a sulfate ion, a hydrogensulfate ion, a sulfite ion, a nitrate ion or a phosphate ion, or a conjugate base of an organic acid such as a carboxylic acid ion, a sulfonic acid ion or a phosphonic acid ion.

The hydrosilyl-terminated polyoxyethylene represented by formula (I) of the present invention can be prepared, for example, by the following methods. Namely, a commercially available polyoxyethylene of the following formula (IV):

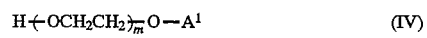

$$\text{H}-(\text{OCH}_2\text{CH}_2)_m-\text{O}-\text{A}^1 \qquad (IV)$$

wherein, $A^1$ is an alkyl group or a hydrogen atom, the average value of degree of polymerization m, is a real number of from 3 to 100; is reacted with a strong base followed by reacting with a alkenyl compound of the following formula (V):

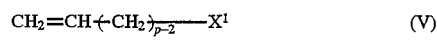

$$\text{CH}_2=\text{CH}-(\text{CH}_2)_{p-2}-X^1 \qquad (V)$$

wherein, $X^1$ is a halogen atom, p is a integer of from 2 to 6; to obtain an alkenyl-terminated polyoxyethylene compound of the following formula (VI):

$$\text{CH}_2=\text{CH}-(\text{CH}_2)_{p-2}-(\text{OCH}_2\text{CH}_2)_m-\text{O}-\text{A}^2 \qquad (VI)$$

wherein, $A^2$ is an alkyl group or a group represented by $-(\text{CH}_2)_{p-2}-\text{CH}=\text{CH}_2$, p is an integer of from 2 to 6, the average value of degree of polymerization, m, is a real number of from 3 to 100. The polyoxyethylene compound of the above formula (VI) is then reacted with a hydrosilane compound of the following formula (VII):

$$X^2-\underset{R^2}{\overset{R^1}{\underset{|}{\overset{|}{Si}}}}-\text{H} \qquad (VII)$$

wherein, each of $R^1$ and $R^2$ which may be the same or different, is an $C_{1-6}$ alkyl group or a phenyl group, and $X^2$ is a halogen atom or a lower alkoxy group; in the presence of a hydrosilylation catalyst to obtain a silyl-terminated polyoxyethylene compound of the following formula (VIII):

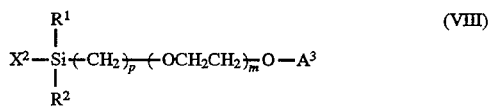

$$X^2-\underset{R^2}{\overset{R^1}{\underset{|}{\overset{|}{Si}}}}-(\text{CH}_2)_p-(\text{OCH}_2\text{CH}_2)_m-\text{O}-\text{A}^3 \qquad (VIII)$$

wherein, each of $R^1$ and $R^2$ which may be the same or different, is a $C_{1-6}$ alkyl group or a phenyl group; $X^2$ is a halogen atom or a lower alkoxy group; $A^3$ is an alkyl group or a group represented by $-(\text{CH}_2)_p-\text{SiR}^1\text{R}^2\text{X}^2$; p is an integer of from 2 to 6; an average value of degree of polymerization, m, is a real number of from 3 to 100; and the halogen atom or the lower alkoxy group on the silyl group in the resulting polyoxyethylene compound of the above formula (VIII) is then hydrolyzed to obtain a hydroxysilyl-terminated polyoxyethylene compound of the above formula (I).

The strong base to be used for the above reaction may, for example, be an organolithium compound such as methyllithium, n-butyllithium, sec-butyllithium, t-butyllithium, phenyllithium, lithium diisopropylamide or lithium bistrimethylsilylamide; an alkali metal hydride such as sodium hydride or potassium hydride, or a Grignard compound such as methylmagnesium iodide, ethylmagnesium bromide or phenylmagnesium bromide. Such a strong base is used usually in an amount of about one equivalent relative to the polyoxyethylene compound of the above formula (IV). The reaction is preferably conducted at a relatively low temperature of from −80° C. to room temperature, in order to suppress a side reaction. Further, this reaction is preferably conducted in an organic solvent. As the solvent to be used here, tetrahydrofuran, dimethoxyethane, dioxane, benzene, toluene or hexane is suitably employed. It is preferred to conduct the reaction in an atmosphere of inert gas such as argon or nitrogen.

As the alkenyl compound represented by the formula (V) may, for example, be vinyl chloride, vinyl bromide, allyl chloride, allyl bromide, allyl iodide, 4-bromobutene, 5-bromopentene, 6-bromohexene. As the hydrosilane compound represented by the formula (VII) may, for example, be dimethylchlorosilane, dimethylmethoxysilane, dimethylethoxysilane, diethylchlorosilane, diethylmethoxysilane, dipropylethoxysilane, diisopropylethoxysilane, dibutylethoxysilane, di-t-butylethoxysilane, dipentylethoxysilane, dihexylethoxysilane, methylpropylmethoxysilane, methylphenylmethoxysilane, diphenylchlorosilane, diphenylmethoxysilane.

As the hydrosilylation catalyst to be used for the reaction of the alkenyl-terminated polyoxyethylene compound of the above formula (VI) and the hydrosilane compound of the above formula (VII) to obtain the polyoxyethylene compound of the above formula (VIII) in the above process, it is most common to employ a platinum type catalyst such as platinum, platinum-carbon, chloroplatinic acid or dicyclopentadienylplatinum dichloride. Besides, it is also possible to employ a metal complex containing palladium or rhodium. For example, $(Ph_3P)_4Pd$, $(Ph_3P)_2PdCl_2$, $(PhCN)_2PdCl_2$, $(Ph_3P)_3RhCl$, $(Ph_2PH)_2RhCl$, $(Ph_3P)_2(CO)RhCl$, or $[(C_2H_5)_3P]_2(CO)RhCl$ may be used as the catalyst. The catalyst may be used usually in an amount of from 1/100 to 1/1,000 equivalent relative to the alkenyl group of the compound of the above formula (VI). To complete the reaction, it is necessary to mix the reactants so that the compound of the above formula (VII) would be at least equimolar to the alkenyl group in the compound of the above formula (VI). This reaction is preferably conducted in a solvent. As such a solvent, hexane, benzene, toluene, acetone, trichloroethylene, carbon tetrachloride, tetrahydrofuran or the like, may be employed. The reaction is conducted usually at a temperature within a range of from 40° to 100° C. and preferably conducted in an atmosphere of an inert gas such as argon or nitrogen.

The hydrolysis for the preparation of the polyoxyethylene compound represented by the above formula (I) of the present invention from the polyoxyethylene compound of the above formula (VIII) is conducted usually in the presence of a basic or acidic substance, whereby the reaction proceeds smoothly. As the basic or acidic substance to be used, it is preferred to employ a basic substance such as lithium hydroxide, potassium hydroxide, sodium hydroxide, aluminum hydroxide, potassium carbonate, sodium carbonate, potassium acetate or sodium acetate, or an acidic substance such as hydrochloric acid, sulfuric acid, nitric acid, acetic acid, calcium sulfate, calcium nitrate or magnesium sulfate. Particularly, it is preferred to employ a weakly basic substance or a weakly acidic substance among the above basic or acidic substances. Such a basic or acidic substance is used preferably within a range of from 0.1 to 5.0 equivalent to the compound of the above formula (VIII). Further, it is necessary to conduct this reaction in the presence of water. An organic solvent soluble in water, such as methanol, ethanol, propanol, acetone, tetrahydrofuran or acetonitrile, may be used in combination, so that the reaction proceeds smoothly. The reaction is usually conducted at around room temperature. If the temperature is high, a disiloxane compound which is a dimer of the desired silanol, may eventually be formed as a by-product. In a case where such a dimerization is likely to proceed, it is necessary to control the reaction temperature within a range of from −100° C. to room temperature in order to suppress the formation of the by-product as little as possible.

On the other hand, a quaternary-salt-terminated polyoxyethylene/polyorganosiloxane block copolymer represented by the above formula (II) of the present invention can be prepared, for example, by the following methods, from the compound of the above formula (I) which is obtainable according to the above procedure. Namely, a hydrosilyl-terminated polyoxyethylene compound of the above formula (I) is reacted with a strong base to produce a silanolate anion followed by reacting with a cyclotrisiloxane compound of the following formula (IX):

wherein, each of $R^3$ and $R^4$ which may be the same or different, is a $C_{1-6}$ alkyl group or a phenyl group; and the reaction is terminated by means of a chlorosilane compound of the following formula (X):

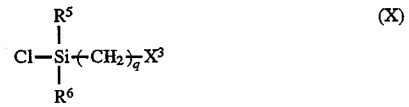

wherein, each of $R^5$ and $R^6$ which may be the same or different, is a $C_{1-6}$ alkyl group or a phenyl group, is a $X^3$ is a halogen atom, q is an integer of from 1 to 6; to obtain a haloalkyl-terminated polyoxyethylene/polyorganosiloxane block copolymer of the following formula (XI):

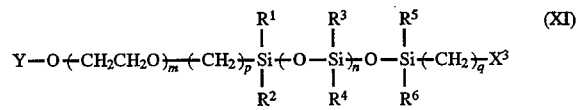

wherein, each of $R^1$ to $R^6$ which may be the same or different, is a $C_{1-6}$ alkyl group or a phenyl group, $X^3$ is a halogen atom, $Y^1$ is an alkyl group or a haloalkyl-terminated organosiloxane chain represented by the following formula (XII):

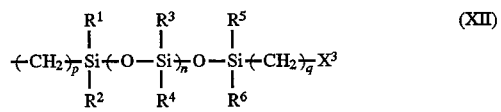

where p is an integer of from 2 to 6, q is an integer of from 1 to 6, an average value of degree of polymerization, m or n, is a real number of from 3 to 100, each of $R^3$ and $R^4$ may be the same or different in each of the repeating unit. Then, the resulting copolymer of the above formula (XI) and the compound of the following formula (XIII):

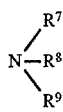

(XIII)

wherein, each of $R^7$ to $R^9$ which may be the same or different, is an alkyl group, a substituted alkyl group or a phenyl group, or two or three of $R^7$ to $R^9$ and the nitrogen atom connected thereto together form a heterocycle containing a nitrogen; are mixed and subjected to quaternization reaction to obtain the quaternary-salt-terminated polyoxyethylene/polyorganosiloxane block copolymer represented by the above formula (II) wherein $X^-$ is a halogen ion. Further, a copolymer of the formula (II) wherein $X^-$ is other than the halogen ion can readily be obtained by ion-exchanging the counter halogen anion of the resulting copolymer of the above formula (II) with a conjugate base of the corresponding mineral acid or organic acid.

The strong base to be used for the above reaction may, for example, be an organolithium compounds such as methyllithium, n-butyllithium, sec-butyllithium, t-butyllithium, phenyllithium, lithium diisopropylamide or lithium bistrimethylsilylamide; an alkali metal hydride such as sodium hydride or potassium hydride, or a Grignard compound such as methylmagnesium iodide, ethylmagnesium bromide or phenylmagnesium bromide. Such a strong base is used usually in an amount of about one equivalent to the hydroxysilyl group in the polyoxyethylene compound of the above formula (I). The reaction is preferably conducted at a relatively low temperature of from −80° C. to room temperature, in order to suppress a side reaction. Further, this reaction is preferably conducted in an organic solvent. As the solvent to be used here, tetrahydrofuran, dimethoxyethane, dioxane, benzene, toluene or hexane is suitably employed. It is preferred to conduct the reaction in an atmosphere of inert gas such as argon or nitrogen.

The cyclotrisiloxane compound of the above formula (IX), which is a monomer for forming a polysiloxane backbone, includes, for example, hexamethylcyclotrisiloxane, hexaethylcyclotrisiloxane, hexapropylcyclotrisiloxane, hexaisopropylcyclotrisiloxane, hexabutylcyclotrisiloxane, hexapentylcyclotrisiloxane, hexahexylcyclotrisiloxane, hexaphenylcyclotrisiloxane, 1,3,5-trimethyl-1,3,5-triethylcyclotrisiloxane, 1,3,5-trimethyl-1,3,5-tri-t-butylcyclotrisiloxane, 1,3,5-trimethyl-1,3,5-tripropylcyclotrisiloxane or 1,3,5-trimethyl-1,3,5-triphenylcyclotrisiloxane. Further, two or more of such cyclotrisiloxane compounds may be used in combination at the reaction.

The chlorosilane compound of the above formula (X) to be used as a terminating agent may, for example, be chloromethyldimethylchlorosilane, bromomethyldimethylchlorosilane, iodomethyldimethylchlorosilane, 2-chloroethyldimethylchlorosilane, 3-chloropropyldimethylchlorosilane, 3-bromopropyldimethylchlorosilane, 3-iodopropyldimethylchlorosilane, 4-chlorobutyldimethylchlorosilane, 5-chloropentyldimethylchlorosilane, 6-chlorohexyldimethylchlorosilane, 3-chloropropyldiethylchlorosilane, 3-bromopropyldipropylchlorosilane, 3-chloropropyldibutylchlorosilane, 3-chloropropyldihexylchlorosilane, 3-chloropropylmethylethylchlorosilane, 3-chloropropylmethylpropylchlorosilane, 3-chloropropylmethylisopropylchlorosilane, 3-chloropropylmethyl-t-butylchlorosilane, 3-chloropropylmethylbutylchlorosilane, 3-chloropropylmethylphenylchlorosilane or 3-chloropropyldiphenylchlorosilane.

By adjusting the amount of cyclotrisiloxane compound of the above formula (IX) in the above process, it is possible to control the degree of polymerization, n, of the haloalkyl-terminated polyoxyethylene/polyorganosiloxane block copolymer of the above formula (XI) and the quaternary-salt-terminated polyoxyethylene/polyorganosiloxane block copolymer of the above formula (II) of the present invention. In this case, however, the observed degree of polymerization is indicated as an average value (a real number), because the copolymer of the above formula (II) or (XI) is a mixtures of polyorganosiloxanes having different degrees of polymerization, n. In order to control this degree of polymerization, n, to a level of at least 3 on the average, it is necessary to use the cyclotrisiloxane compound of the above formula (IX) in an amount of at least one equivalent relative to the silanolate anion used as the initiator.

For the quaternization of the copolymer of the above formula (XI) to prepare the copolymer of the above formula (II), it is preferred to employ a solvent. The solvent may, for example, be hexane, benzene, toluene, diethyl ether, dioxane, tetrahydrofuran, acetone, methyl ethyl ketone, chloroform, methylene chloride, N,N-dimethylformamide, N,N-dimethylacetamide, dimethylformamide, dimethylformamide or N-methylpyrrolidone. The reaction proceeds smoothly within a range of from 0° to 100° C., preferably from 20° to 80° C. In addition, when the terminal halogen atom represented by $X^3$ in the starting copolymer of the above formula (XI) is a chlorine atom, the above quaternization is hard to proceed. Therefore, in this case, it is preferred to conduct the quaternization after exchanging the terminal chlorine atom to bromine atom or iodine atom by means of sodium bromide or sodium iodide.

The compound of the above formula (VIII) to be used in the quaterization may, for example, be trimethylamine, triethylamine, tripropylamine, triisopropylamine, tributylamine, triisobutylamine, tripentylamine, trihexylamine, dimethylethylamine, dimethylpropylamine, dimethylisopropylamine, dimethylbutylamine, dimethylhexylamine, methyldiethylamine, N,N-dimethylaniline, N,N-diethylaniline, N,N-dipropylaniline, N,N-dibutylaniline, N,N-dipentylaniline, N,N-dihexylaniline, N-methyl-N-ethylaniline, N-methyl-N-propylaniline, N-methyl-N-butylaniline, N-methyl-N-hexylaniline, N,N-dimethyl-2-naphtylamine, N,N-dimethylbenzylamine, N,N-diethylbenzylamine, N,N-dimethylethanolamine, 1-methylpyrrolidine, 1-methyl-3-pyrolidinol, 1-methyl-3-pyrrolidineethanol, 1-methylpiperidine, 1-methyl-2-piperidineethanol, 4-methylmorpholine, 3-methylthiazole, 1-methylindole, pyridine, α-picoline, β-picoline, γ-picoline, 3,5-dimethylpyridine, 2,4-dimethylpyridine, 2,6-dimethylpyridine, 2,4,6-trimetylpyridine, 4-ethylpyridine, 4-propylpyridine, 4-isopropylpyridine, 4-butylpyridine, 4-t-butylpyridine, 4-pentylpyridine, 4-hexylpyridine, 2-methyl-4-t-butylpyridine, 4-methyl-2,6-di-t-butylpyridine, 2-phenylpyridine, 3-phenylpyridine, 4-phenylpyridine, 4-methyl-2-phenylpyridine, 5-methyl-2-phenylpyridine or 4-methyl-2,6-diphenylpyridine.

The quaternary-salt-terminated polyoxyethylene/polyorganosiloxane block copolymer of the above formula (II) of the present invention, which is obtainable by the above process, can be used as an agent for promoting percutaneous absorption of a drug. Since this copolymer has a quaternary salt as a polar group, a polyoxyethylene chain as another hydrophilic group and a polyorganosiloxane chain as a hydrophobic group, the copolymer shows characteristics as a surfactant. Therefore, in addition to the use as an agent for promoting percutaneous absorption of a drug, the copolymer of the present invention may be used as a cleaning agent, a germicide, an antiseptic, a cosmetic, etc. When it is used as an agent for promoting percutaneous absorption of a drug, its average value of degree of polymerization affects the promoting effects substantially. In order to obtain high promoting effects, each average value of the degrees of polymerization represented by m and n in the above formula (II), is preferably within a range of from 3 to 100, more preferably within a range of from 3 to 50, although the preferable range varies depending upon the drug to be used.

The agent for promoting percutaneous absorption of a drug, which comprises the quaternary-salt-terminated polyoxyethylene/polyorganosiloxane of the above formula (II) of the present invention, is used as a preparation (a composition) for percutaneous absorption of drugs, by mixing with a drug and a pharmaceutically acceptable carrier and/or an additive. As concrete examples, the agent may be used in an optional form such as tincture wherein the copolymer is dissolved in a solvent such as water or an alcohol together with a drug, or an ointment or cream wherein it is mixed together with the drug in an ointment or cream base, or a tape formulation prepared by incorporating it together with the drug in a polymer film or in an adhesive. The content of the copolymer or the percutaneous absorption-promoting agent of the present invention in the preparation varies depending upon the mode of its use. However, it is usually within a range of from 0.1 to 50% by weight, preferably from 1 to 20% by weight. If the content is small, the absorption-promoting effects tend to be small. On the other hand, if it is large, side effects such as skin irritation tend to be remarkable, and the release of the drug may sometimes be suppressed.

The drug to be used in the present invention may be a drug for human or for animals. It includes, for example, antiphlogistic analgesics such as acetaminophene, aspirin, methyl salicylate, choline salicylate, glycol salicylate, 1-menthol, camphor, mephenamic acid, furphenamic acid, antipyrine, indomethacin, diclofenac, diclofenac sodium, alclofenac, ibuprofen, ketoprofen, naproxen, pranoprofen, fenoprofen, fenprofen, flurbiprofen, indoprofen, fentiazac, tolmetin, suprofen, benzadac, bufexamac, piroxicam, phenylbutazone, oxyphenbutazone, clofezone, pentazocine and mepirizol; steroid antiphlogistics such as hydrocortisone, predonisolone, dexamethasone, triamcinolone acetonide, fluocinolone acetonide and fludrocortisone acetate; antihistamine or antiallergic agents such as chlorpheniramine, glycyrrhetnic acid, diphenhydramine and periactin; local anesthetics such as benzocaine, procaine, dibucaine and lidocaine; antibacterial agents including tetracyclines such as chlorotetracycline, penicillins such as ampicillin, cephalosporins such as cephalothin, aminoglycosides such as kanamycin, macrolides such as erythromycin, chloramphenicol, iodide compounds, nitrofurantoin, nystatin, amphotericin, fradiomycin, sulfonamides, pyrrole nitoline, clotrimazole and nitrofurazone; antihypertensives such as clonidine, α-methyldopa, reserpine, syrosingopine, recinamin, cinnarizine, hydrazine and prazosin; depressor diuretics such as theophylline, trichloromethiazide, furosemide, tripamide, methyclothiazide, penfultizide, hydrocyazide, spironolactone and metolazone; cardiacs such as digitalis, ubidecarenon and dopamine; coronary vasodilators such as nitroglycerine, isosorbitol dinitrate, erythrityl tetranitrate, pentaerythrityl tetranitrate, dipyridamole, dilazep, trapidil and trimethadizine; vasoconstrictors, such as dihydroergotamine, and dihydroergotoxine; β-blocker or antiarrhythmic agents such as pindol and propranolol hydrochloride; calcium antagonists such as diltiazem, nifedipine, nicardipine, verapamil, bencyclane and dilazep; antiepileptics such as nitroazepam, meprobamate and phenytoin; antivertigo agents such as isoprenaline, betahistine and scopolamine; tranquilizers such as diazepam, lorazepam, flunitrazepam and fluphenazine; hypo-sedatives such as phenobarbital, amobarbital and cyclobarbital; muscle relaxants such as triperizone, bacrophen, dantrolene sodium and cyclobenzapirin; drugs for automatic nerve such as atropine and levodopa; drugs for respiratory organ such as codeine, ephedrine, isoproterenol, dextromethorphan, olecypronaline, ipratropium bromide and cromoglicic acid; hormone or antihormone agents such as corticortropin, oxytocin, vasopressin, testosterone, progesterone, estradiol, salivary gland hormone, thyroid hormone, adrenal hormone, kallikrein, insulin and oxendolone; vitamins such as vitamins A, B, C, D, E and K and their derivatives, calciferols and mecobalamin; antitumor agents such as 5-fluorouracil and its derivatives, adriamycin, krestin, picibanil, ancitabine and cytarabine; enzymes such as urokinase; Chinese medicines or crude drugs such as alycyrrhiza, aloe and lithospermum root; antiulcer agents such as allantoin, aldioxa and alcloxa; and others such as prostaglandins and antidiabetic agents. These drugs may be used in combination as a mixture of two or more, as the case requires.

The above drug preparation (composition or formulation) containing the block copolymer of the present invention can be applied to the skin or the mucous membrane (oral cavity, nasal cavity, rectum or vagina) of various parts of a human body by coating or pasting a necessary amount depending upon the particular purpose, thereby an absorption of a drug through the skin or the mucous membrane is promoted. For example, for local treatment of an injury, skin ulcer, muscle pain or arthritis, the preparation may be applied directly to the affected part or to a vicinity thereof. For systemic treatment of an internal organ, it is preferably applied to a site where the drug is readily absorbed (for example at a site where keratin is not developed). Further, when it is used as a cosmetic, the drug formulation may be used as it is or as blended with a known cosmetic component for the purpose of e.g. cleaning or masking the skin, preventing sun burn or skin roughening, or moisturizing the skin.

BEST MODE FOR CARRYING OUT THE INVENTION

Now, the present invention will be described in further detail with reference to Examples and Comparative Examples. However, it should be understood that the present invention is by no means restricted by such specific Examples. In the following reaction formulas and description, $D_3$ represents hexamethylcyclotrisiloxane.

EXAMPLE 1

Synthesis of a hydroxysilyl-terminated polyoxyethylene 1

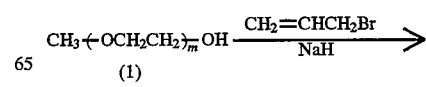

(1)

-continued

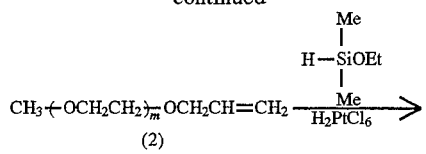
(2)

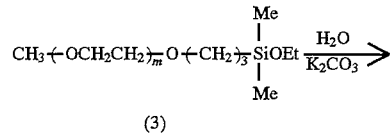
(3)

$$CH_3(OCH_2CH_2)_{\overline{m}}O(CH_2)_{\overline{3}}\underset{Me}{\overset{Me}{\underset{|}{\overset{|}{Si}}}}OH$$
(4)

Under an argon atmosphere, 6.4 g (160 mmol) of sodium hydride in oil was washed with hexane, and 500 ml of tetrahydrofuran solution containing 100.0 g (130 mmol) of commercially available dried methoxy-terminated polyoxyethylene (1) (the average molecular weight: 750, the average degree of polymerization: 17.0) was added to sodium hydride. After the mixture was refluxed for 6 h, 16.1 g (160 mmol) of allyl bromide was added and the whole was further refluxed for 12 h. Then, the solvent was distilled off and 300 ml of ether was added. The salt precipitated was filtered off and the filtrate was dried over anhydrous sodium sulfate. After the solvent was distilled off, the residue was dried in vacuo at 80° C. for 24 h to afford 93.5 g of an α-methoxy-ω-allyl-terminated polyoxyethylene (2) as a white solid (yield: 88.8%). The structure was confirmed by $^1$H-NMR and IR spectra. Further, the average degree of polymerization, $\overline{m}$, was 16.8, which was calculated from $^1$H-NMR.

$^1$H-NMR, δ, (CD$_3$OD ppm); 3.38 (3H, s, C$\underline{H}_3$O—), 3.67 (4mH, m, (C$\underline{H}_2$C$\underline{H}_2$O)$_m$), 4.03 (2H, m, —C$\underline{H}_2$CH=CH$_2$), 5.30 (2H, m, —CH$_2$CH=C$\underline{H}_2$), 5.95 (1H, m, —CH$_2$C$\underline{H}$=CH$_2$).

IR, (neat, cm$^{-1}$); 2880, 1720, 1460, 1360, 1110, 940, 840.

Under an argon atmosphere, 80.0 g (98.6 mmol) of (2) ($\overline{m}$=16.8) was dissolved in 500 ml of tetrahydrofuran. To this solution, 16.1 ml (117 mmol) of dimethylethoxysilane and 0.3 ml of isopropanol solution of chloroplatinic acid (0.1 mol/l) was added, and the solution was refluxed for 8 h. After the solvent and the excess dimethylethoxysilane were distilled off, the residue was dissolved in 600 ml of water, and 500 ml of an aqueous solution containing 33.7 g (244 mmol) of potassium carbonate was slowly added dropwise thereto under stirring at 0° C. The mixture was stirred at room temperature for 12 h and was extracted with ethyl acetate. The organic layer was dried over anhydrous sodium sulfate, and the solvent was distilled off. Then, the residue was dried in vacuo at 80° C. for 24 h to afford 40.5 g of a hydroxysilyl-terminated polyoxyethylene (4) as a white solid (yield: 44.9%). The structure was confirmed by $^1$H-NMR and IR spectra. Further, the average degree of polymerization, $\overline{m}$, was 16.9, which was calculated from $^1$H-NMR.

$^1$H-NMR, δ, (CD$_3$OD, ppm); 0.05 (6H s, Si—C$\underline{H}_3$) 0.50 (2H m, —C$\underline{H}_2$Si(CH$_3$)$_2$OH), 1.53 (2H, m, —CH$_2$C$\underline{H}_2$CH$_2$Si—), 3.30 (3H, s, C$\underline{H}_3$O—), 3.60 ((4m+2)H, m, (C$\underline{H}_2$C$\underline{H}_2$O)$_m$C$\underline{H}_2$—).

IR, (neat, cm$^{-1}$); 3480 (SiOH), 2880, 1460, 1350, 1300, 1250, 1100, 940, 880, 840, 680.

EXAMPLES 2–4

Synthesis of quaternary-salt-terminated polyoxyethylene/polydimethylsiloxane block copolymers 1–3

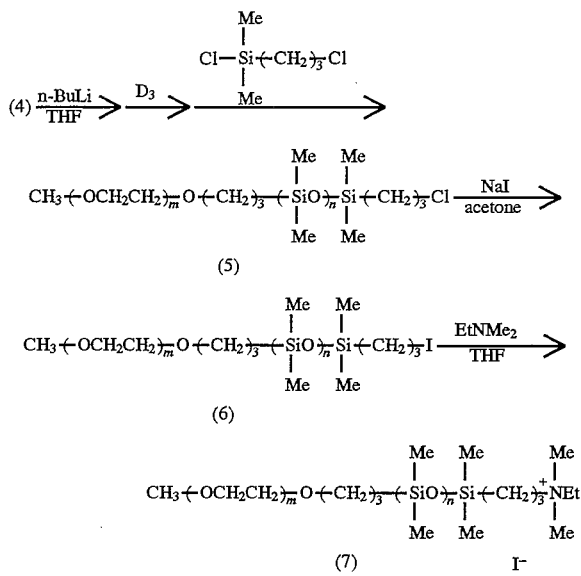

The amount described in Table 1 of (4) ($\overline{m}$=16.9) obtained in Example 1 was dissolved in tetrahydrofuran, and to this solution an equimolar amount of n-butyllithium in hexane (1.6 mol/l) was added at 0° C. The mixture was stirred for 1 h. A tetrahydrofuran solution containing D$_3$ in the amount described in Table 1 was added, and the solution was stirred at room temperature for 12 h. Then, 1.5 equivalent of 3-chloropropyldimethylchlorosilane relative to (4) was added and the mixture was stirred for 3 h. After the solvent was distilled off, water was added thereto and the whole was extracted with ether. The organic layer was dried over anhydrous sodium sulfate, and the solvent was distilled off. Then, the residue was dried in vacuo at 150° C. for 3 h to afford a chloropropyl-terminated polyoxyethylene/polydimethylsiloxane block copolymer (5) in the amount described in Table 1 as a pale yellow viscous solid. The structure was confirmed by $^1$H-NMR spectrum. Further, the average degrees of polymerization of polyoxyethylene and polyorganosiloxane were listed in Table 1, which were calculated from $^1$H-NMR spectrum.

$^1$H-NMR, δ, (CDCl$_3$ ppm); 0.05 ((6n+6)H, s, Si—C$\underline{H}_3$), 0.60 (4H, m, —Si(CH$_3$)$_2$C$\underline{H}_2$—), 1.80 (4H, m, —CH$_2$C$\underline{H}_2$CH$_2$Si—), 3.38 (5H, m, C$\underline{H}_3$O— and —C$\underline{H}_2$Cl), 3.60 ((4m+2)H, m, (C$\underline{H}_2$C$\underline{H}_2$O)$_m$C$\underline{H}_2$—).

TABLE 1

| Example No. | Amount of (4) (g) | Amount of n-BuLi (ml) | Amount of D₃ (g) | Yield of ~(5) (g) | Average degree of polymerization m̄ | Average degree of polymerization n̄ |
|---|---|---|---|---|---|---|
| 2 | 4.0 | 3.9 | 2.6 | 4.7 | 16.9 | 10.9 |
| 3 | 4.0 | 3.9 | 4.3 | 5.8 | 16.9 | 15.2 |
| 4 | 7.0 | 4.9 | 12.2 | 17.0 | 16.9 | 24.2 |

(5) (m̄=16.9) and sodium iodide, the amounts being described in Table 2, were dissolved in acetone and the mixture was refluxed for 48 h. After the solvent was distilled off, water was added thereto and the whole was extracted with ether. The organic layer was dried over anhydrous sodium sulfate, and the solvent was distilled off. Then, the residue was dried in vacuo for 12 h to afford an iodopropyl-terminated polyoxyethylene/polydimethylsiloxane block copolymer (6) in the amount described in Table 2 as a pale yellow viscous solid. The structure was confirmed by ¹H-NMR spectrum. Further, the average degrees of polymerization of polyoxyethylene and polyorganolsiloxane were listed in Table 2, which were calculated from ¹H-NMR spectrum.

¹H-NMR, δ, (CDCl₃, ppm); 0.05 ((6n+6)H, s, Si—C$\underline{H}_3$), 0.63 (4H, m, —Si(CH₃)₂C$\underline{H}_2$—), 1.33 (4H, m, —CH₂C$\underline{H}_2$CH₂Si—), 3.20 (2H, t, —C$\underline{H}_2$I), 3.40 (3H, s, C$\underline{H}_3$O—), 3.65 ((4m+2)H, m, (C$\underline{H}_2$C$\underline{H}_2$)$_m$C$\underline{H}_2$—).

TABLE 2

| Example No. | Amount of (5) (g) | Amount of NaI (g) | Yield of (6) (g) | Average degree of polymerization m̄ | Average degree of polymerization n̄ |
|---|---|---|---|---|---|
| 2 | 2.5 | 1.2 | 2.4 | 16.9 | 11.8 |
| 3 | 2.5 | 1.0 | 2.3 | 16.9 | 16.8 |
| 4 | 17.0 | 4.6 | 15.7 | 16.9 | 27.0 |

TABLE 3

| Example No. | Amount of (6) (g) | Amount of EtNMe₂ (g) | Yield of (7) (g) | Average degree of polymerization m̄ | Average degree of polymerization n̄ |
|---|---|---|---|---|---|
| 2 | 5.0 | 2.1 | 5.4 | 16.9 | 9.2 |
| 3 | 1.3 | 0.4 | 1.3 | 16.9 | 16.8 |
| 4 | 14.0 | 2.5 | 14.8 | 16.9 | 21.5 |

EXAMPLE 5

Synthesis of quaternary-salt-terminated polyoxyethylene/polydimethylsiloxane block copolymer 4

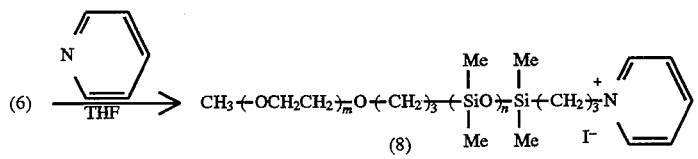

(6) (m̄=16.9) and N,N-dimethylethylamine, the amounts of which were described in Table 3, were dissolved in tetrahydrofuran and the mixture was refluxed for 12 h. After the excess N,N-dimethylethylamine and the solvent were distilled off, the residue was dried in vacuo for 12 h to afford an ammonium-salt-terminated polyoxyethylene/polydimethylsiloxane block copolymer (7) in the amount described in Table 3 as a pale yellow viscous solid. The structure was confirmed by ¹H-NMR and IR spectra. Further, the average degrees of polymerization of polyoxyethylene and polyorganosiloxane were listed in Table 3, which were calculated from ¹H-NMR spectrum.

¹H-NMR, δ, (CDCl₃, ppm); 0.05 ((6n+6)H, s, Si—C$\underline{H}_3$), 0.65 (4H, m, —Si(CH₃)₂C$\underline{H}_2$—), 1.40 (7H, m, —CH₂C$\underline{H}_2$CH₂Si— and NCH₂C$\underline{H}_3$), 3.65 ((4m+15)H, m, C$\underline{H}_3$O—, (C$\underline{H}_2$C$\underline{H}_2$O)$_m$C$\underline{H}_2$— and —C$\underline{H}_2$N(CH₃)₂C$\underline{H}_2$—).

IR, (neat, cm⁻¹); 2980, 2900, 1740, 1460, 1420, 1360, 1260, 1100, 1030, 880, 710.

To 15 ml of tetrahydrofuran solution containing 1.0 g (0.5 mmol) of (6) (the average degrees of polymerization of polyoxyethylene and polyorganosiloxane were m̄=16.9 and n̄=16.8, respectively) obtained in Example 3 was added 3 ml of pyridine and the mixture was refluxed for 12 h. After the excess pyridine was distilled off, the residue was dried in vacuo for 12 h to afford 1.0 g of a pyridinium-salt-terminated polyoxyethylene/polydimethylsiloxane block copolymer (8) as a yellow viscous solid. (Yield: 96.0%, the average degrees of polymerization of polyoxyethylene and polyorganosiloxane were m̄=16.9 and n̄=13.7, respectively) The structure was confirmed by ¹H-NMR and IR spectra.

¹H-NMR, δ, (CDCl₃, ppm); 0.05 ((6n+6)H, s, Si—C$\underline{H}_3$), 0.60 (4H, m, —Si(CH₃)₂C$\underline{H}_2$—), 1.72 (4H, m, —CH₂C$\underline{H}_2$CH₂Si—), 3.65 ((4m+5)H, m, CH₃O— and (C$\underline{H}_2$C$\underline{H}_2$O)$_m$C$\underline{H}_2$—), 4.93 (C$\underline{H}_2$N), 8.17, 8.56, 9.32 (5H, m, pyridine).

IR, (neat, cm$^{-1}$); 2950, 2870, 1630, 1480, 1440, 1350, 1260, 1100–1000, 800.

EXAMPLE 6

Synthesis of hydroxysilyl-terminated polyoxyethylene 2

As described in Example 1, under an argon atmosphere, 10.0 g (250 mmol) of sodium hydride in oil was washed with hexane, and 500 ml of tetrahydrofuran solution containing 80.0 g (228 mmol) of commercially available dried methoxy-terminated polyoxyethylene (1) (the average molecular weight: 350, the average degree of polymerization: 8.0) was added to the sodium hydride. After the mixture was stirred for 6 h, 30.4 g (251 mmol) of allyl bromide was added and the mixture was refluxed for 12 h. Then, the solvent was distilled off and 300 ml of ether was added thereto. The salt precipitated was filtered off and the filtrate was dried over anhydrous sodium sulfate. After the solvent was distilled off, the residue was dried in vacuo at 80° C. for 24 h to afford 84.6 g of an α-methoxy-ω-allyl-terminated polyoxyethylene (2) as a transparent liquid (yield: 95.1%). The structure was confirmed by $^1$H-NMR and IR spectra. Further, the average degree of polymerization, $\bar{m}$, was 8.2, which was calculated from $^1$H-NMR spectrum. The IR spectrum of the product was identical with that in Example 1.

$^1$H-NMR, δ, (CDCl$_3$, ppm); 3.48 (3H, s, C$\underline{H}_3$O—), 3.70 (4mH, m, (C$\underline{H}_2$C$\underline{H}_2$O)$_m$), 4.05 (2H, m, —C$\underline{H}_2$CH=CH$_2$), 5.24 (2H, m, —CH$_2$CH=C$\underline{H}_2$), 5.95 (1H, m, —CH$_2$C$\underline{H}$=CH$_2$).

Under an argon atmosphere, 80.0 g (188 mmol) of (2) ($\bar{m}$=8.2) was dissolved in 500 ml of tetrahydrofuran. To this solution, 23.5 g (225 mmol) of dimethylethoxysilane and 0.2 ml of isopropanol solution of chloroplatinic acid (0.1 mol/l) was added, and the mixture was refluxed for 8 h. After the solvent and the excess dimethylethoxysilane were distilled off, the residue was diluted by adding 800 ml of water and 200 ml of methanol. Then, 200 ml of an aqueous solution containing 31.0 g (225 mmol) of potassium carbonate was slowly added dropwise thereto under stirring at 0° C. After the mixture was stirred at room temperature for 12 h, the methanol was distilled off and the residue was extracted with ether. The organic layer was dried over anhydrous sodium sulfate, and the solvent was distilled off. Then, the residue was dried in vacuo at 80° C. for 24 h to afford 79.0 g of a hydroxysilyl-terminated polyoxyethylene (4) as a transparent liquid (yield: 90.2%). The structure was confirmed by $^1$H-NMR and IR spectra. Further, the average degree of polymerization, $\bar{m}$, was 8.4, which was calculated from $^1$H-NMR spectrum. The IR spectrum of the product was identical with that in Example 1.

$^1$H-NMR, δ, (CDCl$_3$ ppm); 0.05 (6H, s, Si—C$\underline{H}_3$), 0.55 (2H, m, —C$\underline{H}_2$Si(CH$_3$)$_2$OH), 1.58 (2H, m, —CH$_2$C$\underline{H}_2$CH$_2$Si—), 3.40 (3H, s, C$\underline{H}_3$O—), 3.65 ((4m+2)H, m, (C$\underline{H}_2$C$\underline{H}_2$O)$_m$C$\underline{H}_2$—).

EXAMPLES 7–9

Synthesis of quaternary-salt-terminated polyoxyethylene/polydimethylsiloxane block copolymers 5–7

The amount described in Table 4 of (4) ($\bar{m}$=8.4) obtained in Example 6 was dissolved in tetrahydrofuran, and to this solution, an equimolar amount of n-butyllithium in hexane (1.6 mol/l) was added at 0° C. The mixture was stirred for 1 h. A tetrahydrofuran solution containing D$_3$ in the amount described in Table 4 was added, and the whole was stirred at room temperature for 12 h. Then, 1.5 equivalent of 3-chloropropyldimethylchlorosilane relative to the polyoxyethylene was added and the mixture was stirred for 3 h. After the solvent was distilled off, water was added to the solution and the whole was extracted with ether. The organic layer was dried over anhydrous sodium sulfate, and the solvent was distilled off. Then, the residue was dried in vacuo for 3 h to afford a chloropropyl-terminated polyoxyethylene/polydimethylsiloxane block copolymer (5) in the amount described in Table 4 as a pale yellow liquid. The structure was confirmed by $^1$H-NMR spectrum. Further, the average degrees of polymerization of polyoxyethylene and polyorganosiloxane of the copolymers were listed in Table 4, which were calculated from $^1$H-NMR spectrum.

$^1$H-NMR, δ, (CDCl$_3$, ppm); 0.05 ((6n+6)H, s, Si—C$\underline{H}_3$), 0.58 (4H, m, —Si(CH$_3$)$_2$C$\underline{H}_2$—), 1.70 (4H, m, —CH$_2$C$\underline{H}_2$CH$_2$Si—), 3.36 (5H, m, C$\underline{H}_3$O— and —C$\underline{H}_2$Cl), 3.62 ((4m+2) H, m, (C$\underline{H}_2$C$\underline{H}_2$O)$_m$C$\underline{H}_2$—).

TABLE 4

| Example No. | Amount of (4) (g) | Amount of n-BuLi (ml) | Amount of D$_3$ (g) | Yield of (5) (g) | Average degree of polymerization $\bar{m}$ | Average degree of polymerization $\bar{n}$ |
|---|---|---|---|---|---|---|
| 7 | 6.0 | 7.5 | 8.0 | 12.4 | 8.4 | 7.0 |
| 8 | 10.0 | 12.5 | 22.2 | 27.6 | 8.4 | 15.2 |
| 9 | 6.0 | 7.5 | 18.7 | 23.3 | 8.4 | 19.5 |

(5) ($\bar{m}$=8.4) and sodium iodide, the amounts being described in Table 5, were dissolved in acetone and the mixture was refluxed for 48 h. After the solvent was distilled off, water was added to the solution and the whole was extracted with ether. The organic layer was dried over anhydrous sodium sulfate, and the solvent was distilled off. Then, the residue was dried in vacuo for 12 h to afford an iodopropyl-terminated polyoxyethylene/polydimethylsiloxane block copolymer in the amount described in Table 5 (6) as a pale yellow liquid. The structure was confirmed by $^1$H-NMR spectrum. Further, the average degrees of polymerization of the obtained copolymers were listed in Table 5, which were calculated from $^1$H-NMR spectrum.

$^1$H-NMR, δ, (CDCl$_3$, ppm); 0.05 ((6n+6)H, s, Si—C$\underline{H}_3$), 0.58 (4H, m, —Si(CH$_3$)$_2$C$\underline{H}_2$—), 1.71 (4H, m, —CH$_2$C$\underline{H}_2$CH$_2$Si—), 3.18 (2H, t, —CH$_2$I), 3.40 (3H, s, C$\underline{H}_3$O—), 3.63 ((4m+2)H, m, (C$\underline{H}_2$C$\underline{H}_2$O)$_m$C$\underline{H}_2$—).

TABLE 5

| Example No. | Amount of (5) (g) | Amount of NaI (g) | Yield of (6) (g) | Average degree of polymerization $\bar{m}$ | Average degree of polymerization $\bar{n}$ |
|---|---|---|---|---|---|
| 7 | 7.0 | 4.9 | 7.0 | 8.4 | 8.5 |
| 8 | 15.0 | 6.7 | 14.6 | 8.4 | 14.8 |
| 9 | 13.0 | 3.8 | 13.0 | 8.4 | 21.0 |

(6) ($\bar{m}$=8.4) and N,N-dimethylethylamine, the amounts being described in Table 6, were dissolved in tetrahydrofuran and the mixture was refluxed for 12 h. After the excess N,N-dimethylethylamine and the solvent were distilled off, the residue was dried in vacuo for 12 h to afford an ammonium-salt-terminated polyoxyethylene/polydimethylsiloxane block copolymer (7) in the amount described in Table 6 as a pale yellow viscous liquid. The structure was confirmed by $^1$H-NMR and IR spectra. Further, the average degrees of polymerization of polyorganosiloxane were listed in Table 6, which were calculated from $^1$H-NMR spectrum.

$^1$H-NMR, δ, (CDCl$_3$, ppm); 0.05 ((6n+6)H, s, Si—C$\underline{H}_3$), 0.50 (4H, m, —Si(CH$_3$)$_2$C$\underline{H}_2$—), 1.42 (7H, m, —CH$_2$C$\underline{H}_2$CH$_2$Si— and NCH$_2$C$\underline{H}_3$), 3.63 ((4m+15)H, m, C$\underline{H}_3$O—, (C$\underline{H}_2$C$\underline{H}_2$O)$_m$C$\underline{H}_2$— and —C$\underline{H}_2$N(CH$_3$)$_2$C$\underline{H}_2$—).

IR, (neat, cm$^{-1}$); 2980, 2920, 1730, 1460, 1420, 1360, 1250, 1100–1000, 880.

TABLE 6

| Example No. | Amount of (6) (g) | Amount of EtNMe$_2$ (ml) | Yield of (7) (g) | Average degree of polymerization $\bar{m}$ | Average degree of polymerization $\bar{n}$ |
|---|---|---|---|---|---|
| 7 | 6.8 | 3.1 | 7.0 | 8.4 | 8.5 |
| 8 | 14.6 | 4.6 | 13.4 | 8.4 | 14.8 |
| 9 | 13.0 | 2.6 | 13.0 | 8.4 | 21.0 |

EXAMPLE 10

Synthesis of hydroxysilyl-terminated polyoxyethylene 3

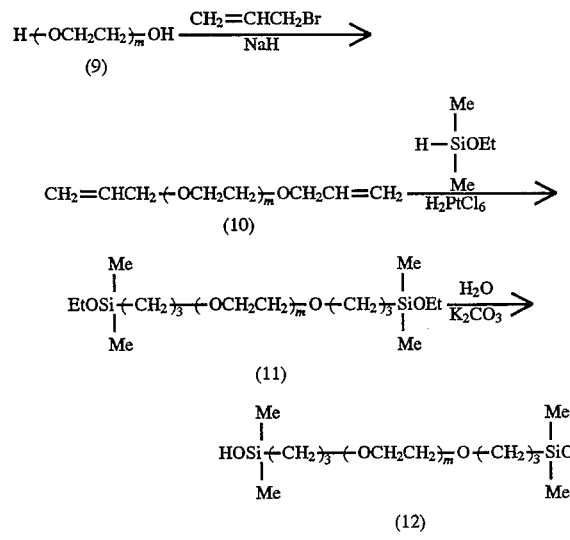

Under an argon atmosphere, 4.8 g (120 mmol) of sodium hydride in oil was washed with hexane, and 200 ml of tetrahydrofuran solution containing 20.0 g (130 mmol) of commercially available dried α,ω-hydroxy-terminated polyoxyethylene (9) (the average molecular weight: 400, the average degree of polymerization: 9.0) was added to the sodium hydride. After the mixture was refluxed for 6 h, 14.6 g (120 mmol) of allyl bromide was added and the whole was refluxed for 12 h. Then, the solvent was distilled off and 300 ml of ether was added to the residue. The salt precipitated was filtered off and the filtrate was dried over anhydrous sodium sulfate. After the solvent was distilled off, the residue was dried in vacuo at 80° C. for 24 h to afford 19.8 g of an α,ω-allyl-terminated polyoxyethylene (10) as a pale yellow liquid (yield: 99.2%). The structure was confirmed by $^1$H-NMR and IR spectra. Further, the average degree of polymerization of polyoxyethylene, $\bar{m}$, was 9.0, which was calculated from $^1$H-NMR spectrum.

$^1$H-NMR, δ, (CDCl$_3$, ppm); 3.50 (4mH, m, (C$\underline{H}_2$C$\underline{H}_2$O)$_m$), 4.03 (4H, m, —C$\underline{H}_2$CH=CH$_2$), 5.27 (4H, m, —CH$_2$CH=C$\underline{H}_2$), 5.90 (2H, m, —CH$_2$C$\underline{H}$=CH$_2$).

IR, (neat, cm$^{-1}$); 2880, 1720, 1460, 1360, 1110, 940, 840.

Under an argon atmosphere, 15.0 g (37.5 mmol) of (10) was dissolved in 200 ml of tetrahydrofuran. To this solution, 15.5 ml (112 mmol) of dimethylethoxysilane and 0.3 ml of isopropanol solution of chloroplatinic acid (0.1 mol/l) was added, and the mixture was refluxed for 12 h. After the solvent and the excess dimethylethoxysilane were distilled off, an α,ω-dimethylethoxy-terminated polyoxyethylene (11) was obtained, the average degree of polymerization being 9.1. 10 g of the α,ω-dimethylethoxy-terminated polyoxyethylene was dissolved in 100 ml of water, and 25 ml of an aqueous solution containing 3.9 g (28.2 mmol) of potassium carbonate was slowly added dropwise thereto under stirring at 0° C. The solution was stirred at room temperature for 12 h and was extracted with ethyl acetate. The organic layer was dried over anhydrous sodium sulfate, and the solvent was distilled off. Then, the residue was dried in vacuo at 80° C. for 24 h to afford 7.8 g of a hydroxysilyl-terminated polyoxyethylene (12) as a pale yellow liquid (yield: 83.5%). The structure was confirmed by $^1$H-NMR and IR spectra. Further, the average degree of polymerization, $\bar{m}$, of the obtained polyoxyethylene was 9.3, which was calculated from $^1$H-NMR spectrum.

$^1$H-NMR, δ, (CDCl$_3$, ppm); 0.05 (12H, s, Si—C$\underline{H}_3$), 0.50 (4H, m, —C$\underline{H}_2$Si(CH$_3$)$_2$OH), 1.50 (4H, m, —CH$_2$C$\underline{H}_2$CH$_2$Si—), 3.39 (4H, t, C$\underline{H}_2$O(CH$_2$CH$_2$O)$_m$C$\underline{H}_2$—), 3.60 (4mH, m, (C$\underline{H}_2$C$\underline{H}_2$O)$_m$).

IR, (neat, cm$^{-1}$); 3480 (SiOH), 2880, 1460, 1350, 1300, 1250, 1100, 940, 880, 840, 680.

EXAMPLE 11

Synthesis of quaternary-salt-terminated polyoxyethylene/polydimethylsiloxane block copolymers 8

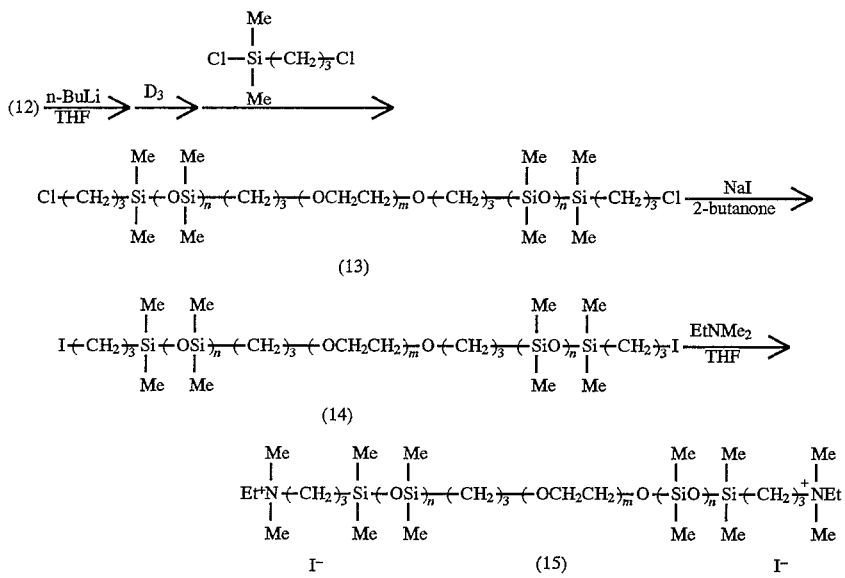

To 50 ml of tetrahydrofuran solution containing 5.0 g (7.6 mmol) of the α,ω-hydroxysilyl-terminated polyoxyethylene (12) ($\bar{m}$=9.3) which was obtained in Example 10 was added under argon atmosphere 9.5 ml (15.2 mmol) of 1.6M n-butyllithium in hexane at 0° C. and the mixture was stirred for 1 h. Further, 50 ml of tetrahydrofuran solution containing 10.1 g (45.5 mmol) of D₃ was added, and the mixture was stirred at room temperature for 12 h. Then, 3.7 ml (22.8 mmol) of 3-chloropropyldimethylchlorosilane was added and the mixture was stirred for 1 h. After the solvent was distilled off, water was added to the solution and the whole was extracted with ether. The organic layer was dried over anhydrous sodium sulfate, and the solvent was distilled off. Then, the residue was dried in vacuo for 12 h to afford 14.7 g of an α,ω-chloropropyl-terminated polyoxyethylene/polydimethylsiloxane block copolymer (13) as a pale yellow liquid (Yield: 75.5%). The structure was confirmed by ¹H-NMR spectrum. Further, the average degree of polymerization of polyorganosiloxane, $\bar{n}$, was 11.9, which was calculated from ¹H-NMR spectrum.

¹H-NMR, δ, (CDCl₃, ppm); 0.05 (2(6n+6)H, s, Si—C$\underline{H}$₃), 0.58 (8H, m, —Si(CH₃)₂C$\underline{H}$₂—), 1.58 (8H, m, —CH₂C$\underline{H}$₂CH₂Si—), 3.25 (4H, t, —C$\underline{H}$₂Cl), 3.40 (4H, t, C$\underline{H}$₂O(CH₂CH₂O)$_m$C$\underline{H}$₂—), 3.60 (4mH, m, (C$\underline{H}$₂C$\underline{H}$₂O)$_m$).

10.0 g (3.9 mmol) of (13) thus obtained and 11.8 g (78.8 mmol) of sodium iodide were added to 100 ml of 2-butanone and the mixture was refluxed for 48 h. After the solvent was distilled off, water was added to the residue and the whole was extracted with ether. The organic layer was dried over anhydrous sodium sulfate, and the solvent was distilled off. Then, the residue was dried in vacuo for 12 h to afford 10.3 g of an α,ω-iodopropyl-terminated polyoxyethylene/polydimethylsiloxane block copolymer (14) as a pale yellow viscous solid (Yield: 93.6%). The structure was confirmed by ¹H-NMR spectrum. Further, the average degree of polymerization of polydimethylsiloxane, $\bar{n}$, was 11.0, which was calculated from ¹H-NMR spectrum.

¹H-NMR, δ, (CDCl₃, ppm); 0.05 (2(6n+6)H, s, Si—C$\underline{H}$₃), 0.58 (8H, m, —Si(CH₃)₂C$\underline{H}$₂—), 1.58 (8H, m, —CH₂C$\underline{H}$₂CH₂Si—), 3.11 (4H, t, —C$\underline{H}$₂I), 3.32 (4H, t, C$\underline{H}$₂O(CH₂CH₂O)$_m$C$\underline{H}$₂—), 3.58 (4mH, m, (C$\underline{H}$₂C$\underline{H}$₂O)$_m$).

To 70 ml of tetrahydrofuran solution containing 5.0 g (1.8 mmol) of (14) thus obtained was added 2.56 g (35 mmol) of N,N-dimethylethylamine, and the mixture was refluxed for 12 h. After the excess N,N-dimethylethylamine and the solvent were distilled off, the residue was dried in vacuo for 12 h to afford 4.91 g of an α,ω-ammonium-salt-terminated polyoxyethylene/polydimethylsiloxane block copolymer (15) as a pale yellow viscous solid (Yield: 96.9%). The structure was confirmed by ¹H-NMR and IR spectra. Further, the average degree of polymerization of polydimethylsiloxane, $\bar{n}$, was 10.8, which was calculated from ¹H-NMR spectrum.

¹H-NMR, δ, (CDCl₃, ppm); 0.05 (2(6n+6)H, s, Si—C$\underline{H}$₃), 0.55 (8H, m, —Si(CH₃)₂C$\underline{H}$₂—), 1.58 (14H, m, —CH₂C$\underline{H}$₂CH₂Si— and NCH₂C$\underline{H}$₃), 3.30 (20H, m, —C$\underline{H}$₂N(C$\underline{H}$₃)₂C$\underline{H}$₂—), 3.61 ((4m+4)H, m, C$\underline{H}$₂O(C$\underline{H}$₂C$\underline{H}$₂O)$_m$C$\underline{H}$₂—).

IR, (neat, cm⁻¹); 2980, 2900, 1740, 1460, 1420, 1360, 1260, 1100, 1030, 880, 710.

EXAMPLES 12, 13

Test for penetration of diclofenac sodium through skin (1)

The skin pealed from the abdominal part of a rabbit was held between two chambers of a two-chamber diffusion cell (effective cross-sectional area: 0.95 cm²). To the donor chamber, 2 ml of a 50% aqueous ethyl alcohol solution containing 20 mg of antiphlogistic diclofenac sodium and a quaternary-salt-terminated polyoxyethylene/polyorganosiloxane block copolymer (percutaneous absorption-promoting agent) (5 wt. %), which was obtained in one of Examples 2 and 3, was introduced, and to the receptor chamber, 2 ml of a phosphate buffer solution adjusted to pH =7.4 was introduced. The temperature was kept at constant by circulating isothermal water at 37° C. in a water jacket around the cell. The two chambers were maintained under stirring, and upon expiration of 6 hours and 12 hours, a portion of the buffer solution was sampled from the receptor chamber, and the permeated diclofenac sodium was quantitatively analyzed by high performance liquid chromatography. The results of the penetration test obtained by using the quaternary-terminated polyoxyethylene/polyorganosiloxane block copolymer, obtained in Examples 2 and 3, as percutaneous absorption-promoting agents, respectively, are shown in Table 7. In Table 7, Comparative Example 1 is the test conducted in the same manner except that no block copolymer was added. As is evident from Table 7, these quaternary-salt-terminated polyoxyethylene/polyorganosiloxane block copolymers exhibit excellent percutaneous absorption-promoting effects to such a hydrophilic drug. Further, the surface of the skin pealed from the abdominal part of the rabbit at the donor chamber site was inspected after the test, whereby no color change was observed in each case, and it was confirmed that no change took place from the state before the test.

TABLE 7

Results of the test for measuring the absorption and penetration of diclofenac sodium by means of the rabbit skin (1). The concentration of the promoting agent; 5% (number of test = 3)*

| Example No. | Copolymer used as a percutaneous absorption-promoting agent | Cumulative penetrated amount after 6 h (mg) | Cumulative penetrated amount after 12 h (mg) |
|---|---|---|---|
| 12 | Example 2 | 0.143 ± 0.009 | 1.444 ± 0.109 |
| 13 | Example 3 | 0.087 ± 0.015 | 0.760 ± 0.103 |
| Comparative Example 1 | none | 0.010 ± 0.003 | 0.042 ± 0.009 |

*The penetrated amount is an average value of the three tests conducted with respect to the skins of three rabbits.

EXAMPLES 14, 15

Test for penetration of diclofenac sodium through skin (2)

The skin pealed from the abdominal part of a rabbit was held between two chambers of a two-chamber diffusion cell (effective cross-sectional area: 0.95 cm$^2$). To the donor chamber, 2 ml of a 50% aqueous ethyl alcohol solution containing 20 mg of antiphlogistic diclofenac sodium and a quaternary-salt-terminated polyoxyethylene/polyorganosiloxane block copolymer (percutaneous absorption-promoting agent) (2 wt. %), which was obtained in one of Examples 2 and 3, was introduced, and to the receptor chamber, 2 ml of a phosphate buffer solution adjusted to pH=7.4 was introduced. The temperature was kept at constant by circulating isothermal water at 37° C. in a water jacket around the cell. The two chambers were maintained under stirring, and upon expiration of 6 hours and 12 hours, a portion of the buffer solution was sampled from the receptor chamber, and the permeated diclofenac sodium was quantitatively analyzed by high performance liquid chromatography. The results of the penetration test obtained by using the quaternary-terminated polyoxyethylene/polyorganosiloxane block copolymer, obtained in Examples 2 and 3, as percutaneous absorption-promoting agents, respectively, are shown in Table 8. In Table 8, Comparative Example 1 is the test conducted in the same manner except that no block copolymer was added. As is evident from Table 8, these quaternary-salt-terminated polyoxyethylene/polyorganosiloxane block copolymers exhibit excellent percutaneous absorption-promoting effects to such a hydrophilic drug. Further, the surface of the skin pealed from the abdominal part of the rabbit at the donor chamber site was inspected after the test, whereby no color change was observed in each case, and it was confirmed that no change took place from the state before the test.

TABLE 8

Results of the test for measuring the absorption and penetration of diclofenac sodium by means of the rabbit skin (2). The concentration of the promoting agent; 2% (number of test = 3)*

| Example No. | Copolymer used as a percutaneous absorption-promoting agent | Cumulative penetrated amount after 6 h (mg) | Cumulative penetrated amount after 12 h (mg) |
|---|---|---|---|
| 14 | Example 2 | 0.183 ± 0.027 | 1.615 ± 0.135 |
| 15 | Example 3 | 0.057 ± 0.008 | 0.493 ± 0.068 |
| Comparative Example 1 | none | 0.010 ± 0.003 | 0.042 ± 0.009 |

*The penetrated amount is an average value of the three tests conducted with respect to the skins of three rabbits.

EXAMPLES 16–22

Test for penetration of antipyrine through skin

The skin pealed from the abdominal part of a rabbit was held between two chambers of a two-chamber diffusion cell (effective cross-sectional area: 0.95 cm$^2$). To the donor chamber, 2 ml of a 50% aqueous ethyl alcohol solution containing 20 mg of antiphlogistic antipyrine and a quaternary-salt-terminated polyoxyethylene/polyorganosiloxane block copolymer (percutaneous absorption-promoting agent) (2 wt. %), which was obtained in one of Examples 2–5, 8, 9 and 11, was introduced, and to the receptor chamber, 2 ml of a phosphate buffer solution adjusted to pH=7.4 was introduced. The temperature was kept at constant by circulating isothermal water at 37° C. in a water jacket around the cell. The two chambers were maintained under stirring, and upon expiration of 6 hours and 12 hours, a portion of the buffer solution was sampled from the receptor chamber, and the permeated antipyrine was quantitatively analyzed by high performance liquid chromatography. The results of the penetration test obtained by using the quaternary-terminated polyoxyethylene/polyorganosiloxane block copolymer, obtained in Examples 2–5, 8, 9 and 11, as percutaneous absorption-promoting agents, respectively, are shown in Table 9. In Table 9, Comparative Example 2 is the test conducted in the same manner except that no block copolymer was added. As is evident from Table 9, these quaternary-salt-terminated polyoxyethylene/polyorganosiloxane block copolymers exhibit excellent percutaneous absorption-promoting effects to such a hydrophilic drug. Further, the surface of the skin pealed from the abdominal part of the rabbit at the donor chamber site was inspected after the test, whereby no color change was observed in each case, and it was confirmed that no change took place from the state before the test.

TABLE 9

Results of the test for measuring the absorption and penetration of antipyrine by means of the rabbit skin. (number of test = 3)*

| Example No. | Copolymer used as a percutaneous absorption-promoting agent | Cumulative penetrated amount after 6 h (mg) | Cumulative penetrated amount after 12 h (mg) |
|---|---|---|---|
| 16 | Example 2 | 0.153 ± 0.004 | 0.638 ± 0.090 |
| 17 | Example 3 | 0.243 ± 0.084 | 0.932 ± 0.308 |
| 18 | Example 4 | 0.353 ± 0.052 | 1.239 ± 0.196 |

TABLE 9-continued

Results of the test for measuring the absorption
and penetration of antipyrine by means of the rabbit skin.
(number of test = 3)*

| Example No. | Copolymer used as a percutaneous absorption-promoting agent | Cumulative penetrated amount after 6 h (mg) | Cumulative penetrated amount after 12 h (mg) |
|---|---|---|---|
| 19 | Example 5 | 0.312 ± 0.071 | 1.186 ± 0.218 |
| 20 | Example 8 | 0.548 ± 0.092 | 2.341 ± 0.085 |
| 21 | Example 9 | 0.425 ± 0.015 | 2.171 ± 0.259 |
| 22 | Example 11 | 0.558 ± 0.069 | 2.229 ± 0.112 |
| Comparative Example 2 | none | 0.069 ± 0.013 | 0.269 ± 0.041 |

*The penetrated amount is an average value of the three tests conducted with respect to the skins of three rabbits.

EXAMPLES 23–28

Test for penetration of indomethacin through skin

The skin pealed from the abdominal part of a rabbit was held between two chambers of a two-chamber diffusion cell (effective cross-sectional area: 0.95 cm$^2$). To the donor chamber, 2 ml of a 50% aqueous ethyl alcohol solution containing 20 mg of antiphlogistic indomethacin and a quaternary-salt-terminated polyoxyethylene/polyorganosiloxane block copolymer (percutaneous absorption-promoting agent) (2 wt. %), which was obtained in one of Examples 2–4 and 7–9, was introduced, and to the receptor chamber, 2 ml of a phosphate buffer solution adjusted to pH=7.4 was introduced. The temperature was kept at constant by circulating isothermal water at 37° C. in a water jacket around the cell. The two chambers were maintained under stirring, and upon expiration of 6 hours and 12 hours, a portion of the buffer solution was sampled from the receptor chamber, and the permeated indomethacin was quantitatively analyzed by high performance liquid chromatography. The results of the penetration test obtained by using the quaternary-terminated polyoxyethylene/polyorganosiloxane block copolymer, obtained in Examples 2–4 and 7–9, as percutaneous absorption-promoting agents, respectively, are shown in Table 10. In Table 10, Comparative Example 3 is the test conducted in the same manner except that no block copolymer was added. As is evident from Table 10, these quaternary-salt-terminated polyoxyethylene/polyorganosiloxane block copolymers exhibit excellent percutaneous absorption-promoting effects to such a hydrophobic drug. Further, the surface of the skin pealed from the abdominal part of the rabbit at the donor chamber site was inspected after the test, whereby no color change was observed in each case, and it was confirmed that no change took place from the state before the test.

TABLE 10

Results of the test for measuring the absorption
and penetration of indomethacin by means of the rabbit skin.
(number of test = 3)*

| Example No. | Copolymer used as a percutaneous absorption-promoting agent | Cumulative penetrated amount after 6 h (mg) | Cumulative penetrated amount after 12 h (mg) |
|---|---|---|---|
| 23 | Example 2 | 0.014 ± 0.003 | 0.060 ± 0.001 |
| 24 | Example 3 | 0.021 ± 0.004 | 0.083 ± 0.009 |
| 25 | Example 4 | 0.016 ± 0.003 | 0.060 ± 0.005 |
| 26 | Example 7 | 0.029 ± 0.005 | 0.104 ± 0.016 |
| 27 | Example 8 | 0.029 ± 0.005 | 0.116 ± 0.020 |
| 28 | Example 9 | 0.028 ± 0.007 | 0.127 ± 0.019 |
| Comparative Example 3 | none | 0.012 ± 0.001 | 0.031 ± 0.003 |

*The penetrated amount is an average value of the three tests conducted with respect to the skins of three rabbits.

Industrial Applicability

A quaternary-salt-terminated polyoxyethylene/polyorganosiloxane block copolymer of the present invention, which is derived from a novel hydroxysilyl-terminated polyoxyethylene compound of the present invention, is useful for a percutaneous absorption-promoting agent which promotes the penetration or the absorption of a drug through the skin. Besides, since the copolymer of the present invention has a characteristic as surfactant, it is possible to apply it to a cleaning agent, germicide, an antiseptic, a cosmetic, and the like.

We claim:

1. A quaternary-salt-terminated polyoxyethylene/polyorganosiloxane block copolymer, of the following formula (II):

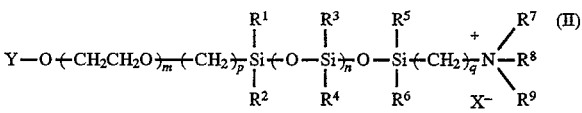

wherein, each of $R^1$ to $R^6$ which may be the same or different, is a $C_{1-6}$ alkyl group or a phenyl group; each of $R^7$ to $R^9$ which may be the same or different, is an alkyl group, a substituted alkyl group or a phenyl group, or two or three of $R^7$ to $R^9$ and the nitrogen atom connected thereto together form a hetero-ring containing a nitrogen; $X^-$ is a counter anion in the quaternary salt; Y is an alkyl group or a quaternary-salt-terminated polyorganosiloxane chain represented by the following formula (III):

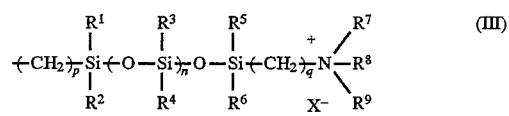

where p is an integer of from 2 to 6; q is an integer of from 1 to 6; an average value of degree of polymerization, m or n, is a real number of from 3 to 100; each of $R^3$ and $R^4$ may be the same or different in each of the repeating unit.

2. A quaternary-salt-terminated polyoxyethylene/polyorganosiloxane block copolymer according to claim 1, wherein the average value of degree of polymerization, m or n, is a real number of from 5 to 50.

3. A composition, comprising:

(a) the polyoxyethylene/polyorganosiloxane block copolymer according to claim 1;

(b) at least one drug; and (c) a pharmaceutically acceptable carrier.

4. The composition according to claim 3, wherein said polyoxyethylene/polyorganosiloxane block copolymer comprises 0.1 to 50% by weight of said composition.

5. A method for promoting the percutaneous absorption of a drug comprising the step of applying an effective amount of the composition according to claim 3 to the skin or a mucous membrane of a patient in need of said drug.

6. A method for promoting the percutaneous absorption of a drug comprising the step of applying an effective amount of the composition according to claim 4 to the skin or a mucous membrane of a patient in need of said drug.

* * * * *